United States Patent [19]
Mishniot

[11] Patent Number: 4,751,236

[45] Date of Patent: Jun. 14, 1988

[54] METHOD FOR TREATING GENITAL HERPES

[76] Inventor: Avihou Mishniot, 301 E. 47th St., New York, N.Y. 10017

[21] Appl. No.: 52,491

[22] Filed: May 20, 1987

[51] Int. Cl.⁴ .............................................. A61K 31/40
[52] U.S. Cl. .................................................... 514/428
[58] Field of Search ........................................ 514/428

[56] References Cited

U.S. PATENT DOCUMENTS 3,342,826  9/1967  Miller et al. ......................... 514/428
4,232,037  11/1980  Florvall et al. ...................... 514/428

FOREIGN PATENT DOCUMENTS 2033900A  5/1980  United Kingdom ................ 514/428

*Primary Examiner*—Jerome D. Goldberg
*Attorney, Agent, or Firm*—Stiefel, Gross & Kurland

[57] ABSTRACT

A method of treating genital herpes and a method useful in preventing recurrent episodes of genital herpes infection is provided.

6 Claims, No Drawings

METHOD FOR TREATING GENITAL HERPES

TECHNICAL FIELD

This invention relates to a method of treating genital herpes and preventing recurrent episodes of genital herpes by treatment with sulpiride, N-(1-Ethylpyrrolidin-2-ylmethyl)-2-methoxy-5-sulphamoylbenzamide.

BACKGROUND OF THE INVENTION

Genital herpes (herpes genitalis) is a disease caused by the herpes simplex virus. There are two types of herpes simplex virus (hereinafter "HSV"); type I and type II. HSV type II is generally associated with genital herpes. However, type I HSV has also been associated with genital herpes. The most common source of the HSV II infection is by venereal contact, although it may also be acquired during birth.

The disease is characterized by groups of watery blisters on mucous membranes. In males these lesions appear as ulcers on glans, prepuce and shaft of the penis. Herpes genitalis on the penis is extremely painful and the condition resolves on its own. In females, the disease is largely asymptomatic and may be characterized only by inflammation. A genital herpes infection may lead to other physiological complications such as urethritis, neuralgia or septic meningitis.

Infection with genital herpes often results in recurrent episodes involving the formation of blisters and sores associated with severe pain and itching. Recurrent HSV II infections are more common in older adults.

There is no known cure for herpes genitalis infections. Therefore, methods of treatment have been directed to treating the clinical manifestations of the disease. For example, topical anesthetics have been used to reduce the pain associated with the infection. Additionally, a method of preventing secondary infections has been employed designed to maintain the lesions in a dry state.

Acyclovir, 9-[(2-hydroxyethoxy)methyl]guanine, U.S. Pat. No. 4,199,574, marketed in the United States by Burroughs Wellcome under the trademark Zovirax ®, is an antiviral drug used in the treatment of herpes viruses. Acyclovir ointment is indicated in the management of *initial* herpes genitalis. Clinical trials of initial herpes genitalis with acyclovir ointment have decreased healing times and, in some cases, decreased the duration of viral shedding and pain, *Physician's Desk Reference*, 41st Ed., p. 814–818 (1987). However, acyclovir is apparently not useful for recurrent herpes.

It is an object of the present invention to provide both a method of treating episodes of genital herpes and a method useful in preventing recurrent episodes.

SUMMARY OF THE INVENTION

In accordance with the present invention, a method of treating episodes of herpes genitalis is provided comprising administering a therapeutically effective oral dosage of sulpiride to the patient. A method useful in preventing recurrent episodes of herpes genitalis infections is further provided.

In particular, it has been found, in accordance with the present invention, that oral administration of an effective amount of sulpiride lessens the severity of episodes of herpes genitalis infections. The pain and itching normally associated with a herpes genitalis episode is decreased. Additionally, the sores and blisters which occur with an episode are drastically reduced in size.

In addition to the preceding advantages, applicant has found in some cases that oral administration of an effective amount of sulpiride over a period of time is useful in preventing recurrent episodes of genital herpes infection.

Sulpiride, the active ingredient employed in the method of the present invention, is a known drug. It is marketed in various countries under different trademarks, such as Abilit (Japan); Dobren (Ravizza, Italy); Miradol (Japan); Tepavil (Prodes, Spain) and others. *Extra Martindale Pharmacopoia*, 28th Edition (1982) p. 1557.

Sulpiride is currently known to exhibit antipsychotic properties, anti-emetic actions, and to inhibit secretions. *Extra Martindale*, supra. Sulpiride is classified by The Merck Index in the following therapeutic categories: antidepressant, digestive aid and psychotropic agent. Sulpiride is indicated in the treatment of psychoses (600–800 mg daily in divided doses IM, followed by 1.2 to 1.6 g daily p.o. and a maintenance dose of 400–800 mg daily); neuroses (in doses of 100–200 mg daily); migraine headaches (100–200 mg daily); and for functional intestinal spasms (150–300 mg daily for gastric and duodenal ulcers). *Extra Martindale*, supra.

Sulpiride is a heterocyclic amino alkyl benzamide compound of the type disclosed in Miller et al U.S. Pat. No. 3,342,826 issued Sept. 19, 1967. Miller discloses the use of sulpiride and like benzamides as antiemetics and in the treatment of mental diseases, in oral dosages of 3 to 150 mg daily in 4 to 6 spaced doses. (Col. 4. lines 49–51).

Sulpiride may be prepared by the method disclosed in Miller et al for benzamido heterocyclic compounds of this type, which method is incorporated herein by this reference.

DETAILED DESCRIPTION

The method of the invention for treating an episode of herpes genitalis comprises the administration to the patient of a therapeutically effective amount of sulpiride. It has been found, in some cases that oral administration of 100 mg of sulpiride three times a day alleviates the clinical manifestations associated with a herpes genitalis episode in one to two days.

The present invention further provides a method useful in preventing recurrent episodes of herpes genitalis. A dosage schedule comprising administering an oral dosage of about 100 mg of sulpiride daily for approximately 30 days, then reducing the dosage to 50 mg daily and maintaining that dosage has been found effective in some clinical instances in preventing recurrent episodes.

The active compound may suitably be administered orally, topically, intraperitoneally, intravenously, or parenterally, oral administration being preferred.

In the methods of the present invention, sulpiride may be administered in admixture with pharmaceutically acceptable substantially nontoxic carriers or excipients, as well recognized by those skilled in the art. As used herein, the term "pharmaceutically acceptable, substantially nontoxic carrier or excipient" includes solvents, dispersing media, coatings, antibacterial agents, isotonic and absorption delaying agents and the like. The use of such agents as carriers or excipients for pharmaceutically active substances is well known in the art. Except insofar as any conventional medium or agent is incompatible with the active ingredient or toxic, its use in the therapeutic formulations of the invention is contemplated. Supplementary active ingredients can also be incorporated in the therapeutic compositions.

The compositions of the invention may be prepared in unit dosage forms for ease of administration and uniformity of dosage. A unit dosage form, as used herein, refers to a physically discrete unit suitable for use as a unitary dosage for the patients to be treated; each unit contains a predetermined quantity of active material calculated to produce the desired therapeutic effect, in association with the required pharmaceutically acceptable carrier.

In one instance, a person suffering from herpes genitalis for a period of 6-7 years and who normally suffered from 4-5 episodes per year varying in severity, was administered sulpiride. His sulpiride treatment consisted of 100 mg per day for 30 days and then 50 mg daily. This treatment regimen was begun while the person was symptom-free and he has remained symptom-free for fourteen months.

Another person suffering from herpes genitalis since approximately 1975, who suffered from frequent episodes occurring approximately every 2-3 months, began oral administration of sulpiride in 1980. For the period of approximately 6-7 years following, he has suffered from approximately only 2-3 episodes. These episodes were of minor severity; when the dosage of sulpiride was increased to 100 mg three times a day, the symptoms were alleviated in one to two days.

What is claimed is:

1. A method of treating herpes genitalis infections in patients infected with herpes genitalis, comprising administering to the patient a dosage of sulpiride effective for the treatment of the infections.

2. The method of claim 1, wherein the dosage of sulpiride is 300 mg per day, administered in 100 mg doses three times a day.

3. The method of claim 1, wherein the sulpiride is admixed with a pharmaceutically acceptable substantially nontoxic carrier.

4. A method useful in preventing recurrent episodes of herpes genitalis infections in patients infected with herpes genitalis, comprising administering to the patient a therapeutically effective dosage of sulpiride.

5. The method of claim 4, wherein the amount of sulpiride administered is 100 mg daily for a period of approximately 30 days, and the dosage is thereafter decreased to a 50 mg daily maintenance dosage.

6. The method of claim 4, wherein the sulpiride is administered in admixture with a pharmaceutically acceptable substantially nontoxic carrier.

* * * * *